(12) United States Patent
Yang et al.

(10) Patent No.: US 12,048,819 B2
(45) Date of Patent: Jul. 30, 2024

(54) METHOD OF FABRICATING A SURGICAL DEVICE

(71) Applicant: IP2IPO Innovations Limited, London (GB)

(72) Inventors: Guang-Zhong Yang, Epsom (GB);
Ning Liu, Shandong (CN); Mohamed E. M. K. Abdelaziz, London (GB);
Burak Temelkuran, London (GB);
Anzhu Gao, Shanghai (CN)

(73) Assignee: IP2IPO Innovations Limited, London (GB)

(*) Notice: Subject to any disclaimer, the term of this patent is extended or adjusted under 35 U.S.C. 154(b) by 744 days.

(21) Appl. No.: 17/261,486

(22) PCT Filed: Jul. 17, 2019

(86) PCT No.: PCT/GB2019/051996
§ 371 (c)(1),
(2) Date: Jan. 19, 2021

(87) PCT Pub. No.: WO2020/016577
PCT Pub. Date: Jan. 23, 2020

(65) Prior Publication Data
US 2021/0316115 A1    Oct. 14, 2021

(30) Foreign Application Priority Data

Jul. 19, 2018 (GB) .................................... 1811823

(51) Int. Cl.
*A61M 25/01* (2006.01)
*A61B 1/008* (2006.01)
(Continued)

(52) U.S. Cl.
CPC .... *A61M 25/0138* (2013.01); *A61M 25/0013* (2013.01); *A61B 1/008* (2013.01); *A61B 2017/00314* (2013.01)

(58) Field of Classification Search
CPC .......... A61M 25/0013; A61M 25/0043; A61M 25/01; A61M 25/0105; A61M 25/0133;
(Continued)

(56) References Cited

U.S. PATENT DOCUMENTS 5,807,241 A    9/1998  Heimberger
7,678,117 B2   3/2010  Hinman
(Continued)

FOREIGN PATENT DOCUMENTS

DE    4317914       12/1994
EP    2581031 A1    4/2013
(Continued)

OTHER PUBLICATIONS

"Attachment", retrieved from http://www.suron.com/laser-cutting-2/laser-cut-tube/, 2 pages, on Aug. 2, 2021.
(Continued)

*Primary Examiner* — Robert A Lynch
(74) *Attorney, Agent, or Firm* — PABST PATENT GROUP LLP

(57) ABSTRACT

A surgical device (204) comprising a first tube (232) having an axis (233) and a wall with a channel extending axially within the wall, the first tube comprising a plurality of integrally-formed interlocking segments (234).

10 Claims, 7 Drawing Sheets

(51) Int. Cl.
*A61B 17/00* (2006.01)
*A61M 25/00* (2006.01)

(58) Field of Classification Search
CPC .......... A61M 25/0138; A61M 25/0147; A61M 2025/0161; A61B 1/0008; A61B 1/0011; A61B 1/005; A61B 1/0051; A61B 1/0055; A61B 1/0057; A61B 1/008; A61B 2017/003; A61B 2017/00305; A61B 2017/00314; A61B 2017/00318
See application file for complete search history.

(56) References Cited

U.S. PATENT DOCUMENTS

| 8,298,161 | B2 | 10/2012 | Vargas | |
|---|---|---|---|---|
| 8,376,865 | B2 | 2/2013 | Forster | |
| 2005/0131279 | A1* | 6/2005 | Boulais | A61B 1/0016 600/141 |
| 2005/0272978 | A1 | 6/2005 | Brunnen | |
| 2005/0212978 | A1 | 9/2005 | Lo | |
| 2015/0164596 | A1 | 6/2015 | Romo | |
| 2016/0067450 | A1 | 3/2016 | Kowshik | |
| 2016/0100942 | A1* | 4/2016 | Morrissey | A61F 2/2436 623/2.11 |
| 2017/0340396 | A1 | 11/2017 | Romo | |
| 2018/0021546 | A1 | 1/2018 | McDermott | |
| 2018/0042451 | A1 | 2/2018 | Cuscuna | |
| 2018/0092517 | A1 | 4/2018 | Graetzel | |

FOREIGN PATENT DOCUMENTS

| EP | 3009104 | 4/2016 |
|---|---|---|
| JP | 2015047453 | 3/2015 |
| WO | 2017213491 | 12/2017 |

OTHER PUBLICATIONS

"Flex Technology", retrieved from http://www.avalign.com/flexible-surgical-instrument-technology.php, 3 pages, on Aug. 2, 2021.
"Flexible Catheter Shafts", retrieved from https://www.pulsesystems.com/flexible-catheter-shafts, 1 page, on Aug. 2, 2021.
"Laser processing", retrieved from https://futaku.co.jp/en/tec0301en/, 6 pages, on Aug. 2, 2021.
"Technical Innovations", retrieved from http://www.creganna.com/technologies/metal-shafts/ innovations/, 2 pages, on Aug. 2, 2021.
International Search Report and Written Opinion for corresponding PCT application PCT/GB2019/051996 dated Oct. 14, 2019.
Liu, et al., "Design and Analysis of a Wire-driven Flexible Manipulator for Bronchoscopic Interventions", 2016 IEEE International Conference on Robotics and Automation (ICRA), 4058-4063 (2016).
Liu, et al., Poster—Design and Kinematics Characterization of a Laser Profiled Continuum Manipulator for the Guidance of Bronchoscopic Instruments (2016).
Search Report for GB181123.2 dated Jan. 22, 2019.
Liu, et al., Movie—"Design And Kinematics Characterization Of A Laser-Profiled Continuum Manipulator for the Guidance of Bronchoscopic Instruments," (2018).
Liu, et al., Poster—"Design and Kinematics Characterization of a Laser Profiled Continuum Manipulator for the Guidance of Bronchoscopic Instruments" (2018).
Liu, et al., Movie—Design and Kinematics Characterization of a Laser Profiled Continuum Manipulator for the Guidance of Bronchoscopic Instruments (2016).

* cited by examiner

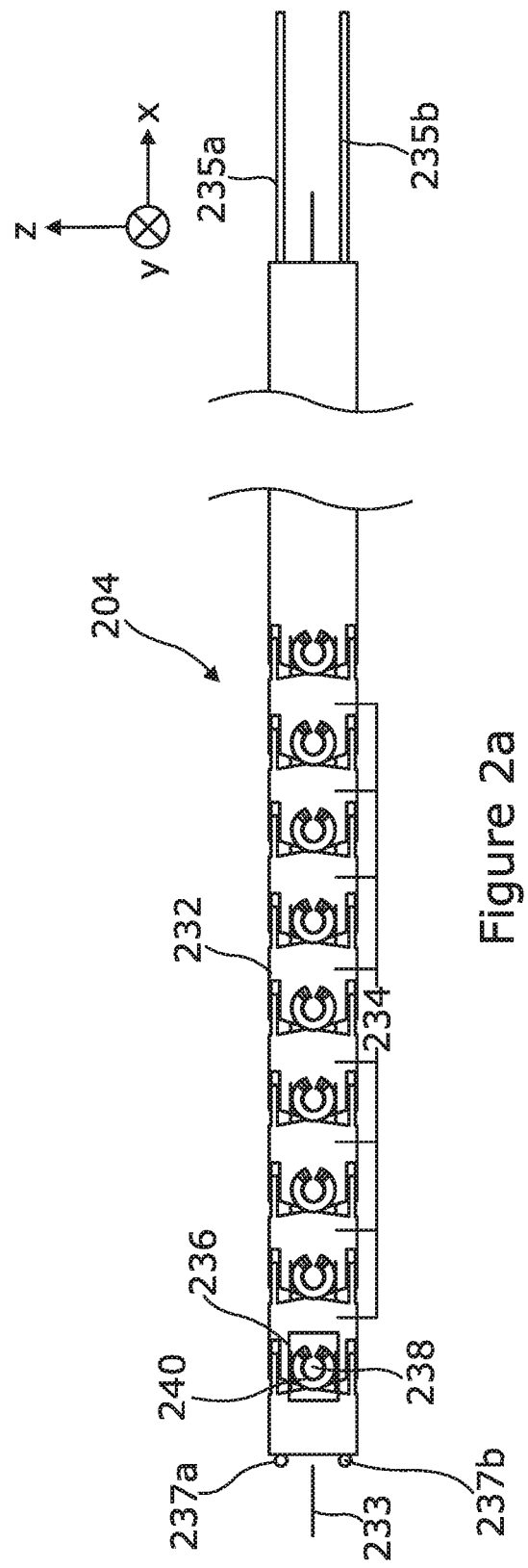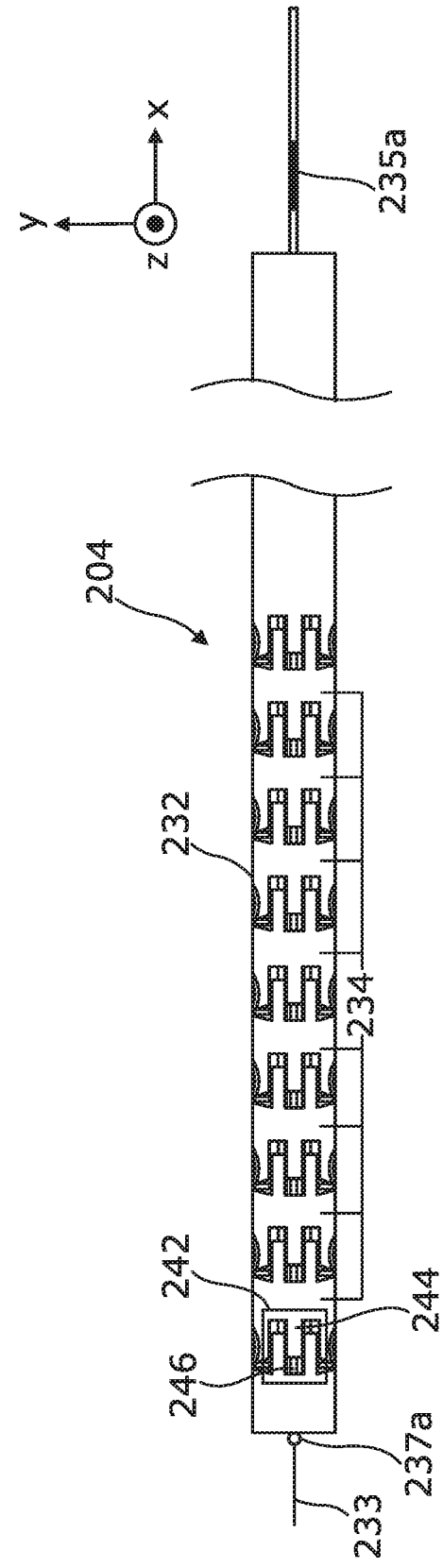

METHOD OF FABRICATING A SURGICAL DEVICE

CROSS-REFERENCE TO RELATED APPLICATIONS

This application is a National Phase application under 35 U.S.C. 371 of PCT/GB2019/051996, filed Jul. 17, 2019, and claims the benefit of and priority to G.B. Application No. 1811823.2, filed Jul. 19, 2018, the disclosures of which are hereby incorporated herein by reference in their entirety.

This invention relates to a surgical device for use in minimally invasive surgery procedures, and to a method of fabricating a surgical device. The invention is particularly directed to a flexible elongated robot for use in bronchoscopic interventions, and to a method of fabricating a robot for use in bronchoscopic interventions. However, the surgical device could be used in other applications, and the method could be used to fabricate similar devices having different applications.

Many minimally invasive surgery (MIS) procedures make use of a flexible tubular guiding device or flexible robot. The flexible tubular device can fit into the working channel of an endoscope and extend into passageways that are too narrow for the endoscope to reach. These passageways could be an artery, airway or intestinal tract, for example.

Bronchoscopy (a clinical routine for lung inspection) is one example of a MIS procedure that can make use of a flexible tubular device. During the procedure, a flexible bronchoscope is inserted through a patient's mouth or nose to examine the interior of their airways. Endobronchial instruments can pass through the working channel of the bronchoscope to perform various functions, for example to take biopsies or deliver implants. It can be challenging for an operator to steer the bronchoscope to peripheral airway regions. A typical bronchoscope can be 6 mm in diameter and restricted from reaching the airways beyond the 4th generation due to the decreasing airway dimensions. These higher generation airways can be accessed by including a flexible tubular device.

The flexible tubular device or flexible robot may comprise a flexible manipulator that can be actuated by a surgeon. Example actuation mechanisms include magnetic actuation and motorised actuation. Wire-driven actuation is another technique wherein one or more antagonistic tendons or filaments can control the bending of the flexible manipulator. The flexible manipulator may comprise a single flexible backbone with tendon-guide discs attached to it. Another option is to assemble multiple segments or vertebra rather than use one single continuum body. Individual segments can comprise guiding features for the tendons. Such assembly of individual segments can complicate manufacturing and add to cost. Another disadvantage with the approach of assembling individual segments, is that they can typically be disassembled. That is, the individual segments are not interlocked in both a tangential and axial direction. As a result, the resulting manipulator can be susceptible to fragmentation, a particularly undesirable result during MIS.

A flexible manipulator should have an outer diameter small enough to fit inside the endoscope and the narrow passageways, and an inner diameter large enough to enable sensors and instruments to pass through. As a result, flexible manipulators often have wall thicknesses in the range of hundreds of microns. Known thin-walled manipulators use additional disc or plate tendon-guide structures and/or tendon-guide features on the interior or exterior surface of the manipulator wall. Such interior/exterior surface features disadvantageously alter the effective inner/outer diameter. Such features and plates also tend to be divided along the axial length of the tube resulting in exposure of, and potential damage to, the tendons in the intervening regions.

A problem with known methods of manufacturing thin-walled wire driven flexible manipulators is therefore that the tendon guide features of the resulting manipulator fail to protect the tendon adequately along the device length, negatively impact the inner or outer diameter and/or require additional components and/or process steps to fabricate.

According to a first aspect of the present disclosure there is provided a surgical device comprising a first tube having an axis and a wall with a channel extending axially within the wall, the first tube comprising a plurality of integrally-formed interlocking segments.

By means of the present invention, a surgical device is provided by a first tube comprising a plurality of interlocking segments and a channel extending axially within a wall of the first tube.

The channel can accommodate a tendon such that the surgical device can function as a wire-driven flexible manipulator. By providing the channel within a wall of the first-tube, the channel does not alter the inner or outer diameter of the surgical device. The inner diameter can advantageously be maximised for instrument accommodation and the outer diameter can be minimised to enable the surgical device to access narrow human passageways, such as bronchi or blood vessels. Furthermore, the outer surface of the surgical device can be kept free from protruding tendon guide features that could cause the device to become lodged in a human passage-way and/or damage the passageway.

By providing the channel within a wall of the first tube, the channel can also protect an accommodated tendon along the length of the first tube. This reduces the risk of tendon fracture during MIS procedures.

The wall of the first tube may be a cylindrical shape or an elliptical shape. In some embodiments the wall may have a multifaceted cross-sectional shape such as a hexagon or octagon or other higher order polygon. The first tube outer diameter may be in the range of 0.5 to 6.0 mm. The first tube inner diameter may be in the range of 0.3 to 5.5 mm The plurality of integrally-formed interlocking segments is arranged as a series of segments, each segment interlocking with adjacent segments. Specific detail of the interlocking mechanism is discussed further below, but the interlocking segments can prevent fragmentation of the surgical device, a particularly undesirable event in MIS procedures. The plurality of interlocking segments can enable bending of the surgical device making it suitable for use as a wire driven flexible manipulator in MIS procedures. A central lumen of the first tube can provide an instrument channel for the surgical device.

In embodiments of the invention, the first tube comprises polymer or glass.

Polymer and glass materials both have the advantages of: (i) being biocompatible and (ii) being compatible with the method of fabricating a surgical device according to the second aspect of the invention. Both materials are also compatible with magnetic resonance imaging (MRI), enabling the use of such techniques during any MIS procedure using the surgical device provided by the method. Silica is an example of a suitable glass material. Suitable polymers include polycarbonate (PC); polysulfone (PSU); poly(methyl methacrylate) (PMMA) (also known as acrylic); and cyclic olefin co-polymer (COC). A specific polymer material may be chosen in relation to further material properties such as elasticity, strength, hardness, brittleness etc.

In embodiments of the invention, the first tube comprises an internal wall.

In such embodiments, the internal wall can divide an internal lumen of the first tube into multiple lumens. The multiple lumens can provide separate instrument channels for the surgical device.

In embodiments of the invention each interlocking segment comprises an axial lock component and a tangential lock component at a first end of the interlocking segment; and a complementary axial lock component and a complementary tangential lock component at a second end of the interlocking segment, wherein: an axial lock component of a first interlocking segment is engageable with a complementary axial lock component of a second interlocking segment to form an axial lock that resists separation of the first segment and the second segment in an axial direction; and a tangential lock component of the first interlocking segment is engageable with a complementary tangential lock component of the second segment to form a tangential lock that prevents separation of the first segment and the second segment in a tangential direction.

In such embodiments of the invention, the interlocking between adjacent interlocking segments is provided by an axial lock and a tangential lock. The axial lock comprises an axial lock component of a first interlocking segment engageable with a complementary axial lock component of a second interlocking segment. The tangential lock comprises a tangential lock component of the first interlocking segment engageable with a complementary lock component of the second interlocking segment.

By providing both an axial lock and a tangential lock, adjacent interlocking segments are fully interlocked and cannot be separated without destructive force.

In embodiments of the invention, each complementary axial lock component comprises a cavity and an opening adjacent to the cavity, wherein a width of the cavity is greater than a width of the opening; and each axial lock component comprises a head and a neck protruding from the head, wherein a width of the neck is less than the width of the opening and a width of the head is greater than the width of the opening and less than the width of the cavity.

In such embodiments, a head of a first axial lock component of a first segment is located within a cavity of a complementary axial lock component of a second segment to form an axial lock. The head of the first axial lock component cannot pass through an opening of the complementary axial lock component due to the width of the head being greater than the width of the opening. This restriction in movement gives rise to the axial interlocking between adjacent interlocking segments. Movement is also restricted in a direction tangential to a surface at the centre of the head and perpendicular to the axis of the first tube.

In some embodiments, the axial lock component further comprises two wings, each wing located on either side of the head and neck and separated by a gap. In such embodiments, the complementary axial lock component further comprises: a C-shaped feature defining an edge of the cavity; and two complementary wing features, with each complementary wing feature located on either side of the C-shape feature. The additional features of the axial lock may give rise to stronger interlocking in the axial and/or tangential directions.

In embodiments of the invention, both the cavity and the head are elliptical, circular or teardrop shaped.

In such embodiments, a head of a lock component in a first interlocking segment can rotate within a cavity of a complementary lock component in a second interlocking segment. As a result, the first interlocking segment can rotate or hinge relative to the second interlocking segment. An axis of rotation (or hinging) is defined as an axis normal to a surface of the head of the axial lock component at a centre point of the head.

The extent of rotation may be limited by a width and/or a shape of a neck of the axial lock component relative to a width and/or a shape of an opening of the complementary axial lock component. In some embodiments the neck of the axial lock component and the opening of the complementary axial lock component both increase in width when moving from a proximal end of the neck/opening, adjacent to the head/cavity, to a distal end of the neck/opening. Such axial lock components and complementary axial lock components may be referred to as keyhole shaped axial locks.

In embodiments of the invention, each complementary tangential lock component comprises a slot; and each tangential lock component comprises a stub with a width less than a width of the slot.

A stub of a tangential lock component of a first interlocking segment, engageable within a slot of a complementary tangential lock component of a second interlocking segment, is restricted from rotating about a static axis. The static axis is defined as an axis normal to a surface of the stub of the tangential lock component at the centre point of the stub. In this way, the first and second interlocking segments cannot rotate or hinge relative to each other about the static axis. The stub/slot design also prevents or restricts relative movement of the first and second segment in a direction tangential to the surface at the centre of the stub and perpendicular to the axis of the first tube.

In some embodiments, the tangential lock component further comprises two slots, each slot located on either side of the stub of the tangential lock component. In such embodiments the complementary tangential lock component further comprises two stubs, each stub located on either side of the slot of the complementary tangential lock component. The additional features of the axial lock may give rise to stronger interlocking in the tangential direction.

In some embodiments the combination of the head-neck/cavity-opening design of the axial lock and the stub/slot design of the tangential lock gives rise to full translational interlocking between adjacent segments. However, any two adjacent segments may rotate relative to each other about the axis of rotation.

In embodiments of the invention, each interlocking segment comprises: a pair of axial lock components; a pair of complementary axial lock components; a pair of tangential lock components; and a pair of complementary tangential lock components.

Each of the pair of axial lock components may be on opposite sides of the surgical device. In a similar way each of the pair of the complementary axial lock components, tangential lock components and complementary tangential lock components may be on opposite sides of the surgical device. By providing pairs of the various locking and complementary locking components the risk of fragmentation of the surgical device, by separation of the segments, can be reduced.

In embodiments of the invention, the axial lock component and the complementary axial lock component of each interlocking segment are axially aligned with one another.

In such embodiments, the axes of rotation between each of the adjacent interlocking segments are parallel with one another. In this way, the axial locks give rise to bending of the surgical device in one degree of freedom, defined by a plane perpendicular to the axes of rotation.

In embodiments of the invention, the axial lock component and the complementary tangential lock component of each interlocking segment are axially aligned with one another.

In such embodiments, the axis of rotation between adjacent segments changes at every axial lock along the surgical device. In this way, the axial locks give rise to bending of the surgical device in two degrees of freedom. This can advantageously enable steering of the surgical device in any direction in a human passage-way.

In embodiments of the invention, the surgical device further comprises a tendon extending through the channel.

The first tube of the surgical device may comprise more than one axial channel and a corresponding tendon or filament for each channel. In this way, the surgical device can be steered through human passage-ways using antagonistic pairs of tendons. The tendons may be secured at a distal end of the first tube. The tendon can be secured to the distal end of the first tube by adhesive or welding, such as laser welding, or mechanical means. The tendon may comprise a ball-head pin to aid adhesion. Tendons may comprise a super-elastic nitinol cable; a liquid crystal polymer (LCP) monofilament or another suitable biocompatible material.

In embodiments of the invention, the surgical device further comprises a tip section interlocked with a distal end of the first tube.

The tip comprises either: (i) an axial lock component and a tangential lock component; or (ii) a complementary axial lock component and a complementary tangential lock component, at a proximal end of the tip. In this way, the tip is engageable with the plurality of interlocking segments. The tip and plurality of interlocking segments are integrally formed from the first tube and can be fabricated by a method according to the second aspect of the invention.

In embodiments of the invention, the surgical device further comprises a second tube at a proximal end of the first tube, the second tube having an axis and a wall with a spiral channel extending along a spiral path within the wall, the spiral path having: a path axis along an axial length of the second tube; and a radius substantially equal to a cross-sectional radius of the second tube.

In such embodiments, the second tube is located at a proximal end of the first tube and may be integral with or affixed to the first tube. In this way, the second tube can operate as a flexible shaft for supporting the first tube which can operate as a wire driven flexible manipulator. An inner diameter and an outer diameter of the second tube may be in the same range values as outlined above in relation to the first tube. The inner diameter and outer diameter of the second tube may be equal to those of the first tube.

The second-tube comprises a spiral channel extending axially within a wall of the second tube. The spiral channel can accommodate a tendon. In some embodiments, there may be more than one spiral channel extending axially within the wall of the second tube. The number of spiral channels may equal the number of channels in the wall of the first tube. When the second tube is bent, the spiral channels remain substantially the same length as each other. This can advantageously reduce the undesirable effects of tendon tensioning and unwanted tendon length changes upon bending of the second tube, which can occur in flexible shafts with straight axial channels.

In embodiments of the invention, the second tube is integrally formed with the first tube.

In embodiments of the invention, the second tube comprises polymer or glass.

The second tube may comprise any of the material options described above in relation to the first tube. The second tube may comprise the same material as the first tube.

In embodiments of the invention, the spiral channel is axially aligned with the channel in the first tube.

By aligning the spiral channel to the axial channel of the first tube, a resulting combined channel can accommodate a tendon. In embodiments with multiple channels in the first tube, a corresponding number of spiral channels are aligned with the first tube channels. The channels can be arranged in pairs on opposite sides of the first tube to accommodate pairs of antagonistic tendons. The second tube can be fabricated by rotating a second preform during a drawing process, as discussed further below in relation to the second aspect of the invention. Providing a second preform with a channel orientation the same as a channel orientation of the first tube can ensure that the resultant spiral channels of the second tube can be aligned with the channels of the first tube. Alternatively, the first tube and second tube may be drawn from a first preform providing a continuous first tube and second tube structure. The spiral channel of the second tube will necessarily be continuous or automatically aligned with the axial channel of the first tube.

According to a second aspect of the present disclosure there is provided a method of fabricating a surgical device comprising the steps of: providing a first preform having an axis and a wall with a channel extending axially within the wall; drawing the first preform to form a first tube having an axis and a wall with a channel extending axially within the wall; and segmenting the first tube into a plurality of interlocking segments.

By means of the present invention, a method is provided for fabricating a surgical device by drawing a first preform into a first tube with a channel extending axially within a wall of the first tube. The first tube is segmented into a plurality of interlocking segments to provide the surgical device. The axial channel within the wall of the tube can provide a tendon guide feature that: (i) protects the tendon for substantially the whole length of the first tube; (ii) does not negatively alter the inner or outer diameter of the first tube; and (iii) requires no additional components or process steps such as channel drilling.

The method according to embodiments of the invention may comprise providing a first preform with more than one channel extending axially within the wall. For example, two or three or four channels may extend axially within the wall of the first preform.

The first preform with a wall and an axial channel can be created within the wall in a number of ways. For example, a rod or bar can be directly machined into a preform comprising a wall. Alternatively, thermoplastic sheets or films can be rolled into a polymer preform comprising a wall. A channel may be drilled into the wall of such preforms to provide the first preform. As a further alternative, a first polymer preform may be manufactured by hot press, cast moulding or injection moulding of thermoplastic pellets and a mould can include a channel feature. Various permutations and combinations of these methods are also possible. Providing a channel in the first preform can be straightforward because the first preform can be several centimetres in diameter and the preform wall thickness can be several millimetres. In some embodiments the first preform diameter may be in the range of 2 to 4 cm.

Drawing a first preform with a channel extending axially within a wall of the first preform produces a smaller-scale first tube of similar design, with a similar scaled channel extending axially within a wall of the first tube. Embodiments comprising preforms with multiple channels will produce first tubes with multiple corresponding scaled channels. In this way, tubes with narrow wall thickness can comprise a channel extending axially within the wall. For example, the first tube may be drawn such that the wall thickness is in the range of 100-1000 microns, and still comprise a channel extending axially within the wall of the first tube. In other words, a first tube can be created with a narrow wall and a channel extending axially within the wall without a step of drilling a hole into the narrow wall. In some embodiments, wherein the surgical device is used with a bronchoscope, the outer diameter of the first tube may be in the range of 1.8 to 2.2 mm; the inner diameter may be in the range of 1.0 to 1.4 mm; and a length of the first tube may be in the range of 15 to 25 mm. Such devices may have a minimum bending radius in the range of 6 to 7 mm.

Segmenting the first tube creates a surgical device with a plurality of interlocking segments without any requirement for assembly of the individual segments. This advantageously reduces the cost and increases the ease of manufacturing of the surgical device compared to methods that require assembly of individual segments.

The plurality of interlocking segments creates an integrally formed surgical device. The interlocking segments prevent separation of the segments (in the absence of a destructive force) and in some embodiments prevent separation in both a tangential and axial direction. The interlocking can be such that adjacent segments may hinge or rotate relative to each other. In this way, the surgical device can be used as a flexible manipulator or flexible robot. The one or more channels in each segment can accommodate tendons to actuate the flexible manipulator. In this way, the surgical device can be used as a flexible manipulator capable of being steered through narrow human passage-ways.

By segmenting the first tube into a plurality of interlocking segments, the axial channel of the first tube is distributed through the plurality of interlocking segments. The axial channel of the first tube retains its integrity and provides a substantially continuous channel to accommodate a tendon.

Segmenting the first tube into a plurality of interlocked segments may be achieved by a variety of processes including laser cutting, mechanical cutting, chemical etching and lithography.

In embodiments of the invention, the step of drawing the first preform comprises drawing the first preform using a fibre drawing process.

In a fibre drawing process, the first preform is placed in a fibre draw tower. A tip of the first preform may be heated and the molten first preform is pulled or drawn out as a first tube fibre (referred to as a neck-down process). During the neck-down process, the viscosity of the preform material, for example polymer or glass, decreases by several orders of magnitude and the first preform necks down under its own weight.

The fibre draw tower may comprise a furnace with one or more heating zones. In some embodiments there may be three heating zones providing a temperature profile along the axial direction of the first preform. The temperature profile may be configured to be at a maximum value in the middle of the profile. The furnace can heat the first preform to a temperature above a glass transition temperature of the first preform material allowing the neck-down process to occur. For polymer preforms, the temperature of the furnace may be in the range of 65° C. to 500° C. For example, for a PC preform, the temperature may be in the range of 145° C. to 400° C. The temperature at the tip of the first preform can define a rapid cooling time, or quenching time, of the first tube fibre as it is drawn from the first preform. Following quenching, a capstan can be used to pull the first tube fibre at a constant speed. In some embodiments the draw speed may be in the range of 0.1 m/min to 10 m/min.

The first tube fibre diameter can be monitored by a laser micrometre. The pulling tension can be monitored using a three-wheel tension sensor, which can measure the effective internal stress inside the first tube fibre. The temperature profile, down-feed speed and draw speed are an adjustable set of parameters that can define the first preform to first tube fibre neck down region. Following completion of the fibre drawing process, a length of the first tube fibre can be cut to form the first tube. The first tube fibre may be used to provide multiple first tubes. In some embodiments, the first tube fibre outer diameter, and first tube outer diameter, may both be in the range of 0.5 to 6.0 mm. The first tube fibre inner diameter, and first tube inner diameter, may be in the range of 0.3 to 5.5 mm.

In embodiments of the invention, the step of segmenting the first tube comprises a mechanical cutting process, a chemical etching process and/or a lithography process.

The step of segmenting the first tube may comprise a laser cutting process, a mechanical cutting process, a chemical etching process, a lithography process or combinations thereof.

In embodiments of the invention, the step of providing a first preform comprises providing a first preform comprising polymer or glass.

Polymer and glass materials both have the advantages of: (i) being biocompatible and (ii) being suitable for fibre drawing. Both materials are also compatible with magnetic resonance imaging (MRI), enabling the use of such techniques during any MIS procedure using the surgical device provided by the embodiment. Silica is an example of a glass suitable for use as the first preform material. Suitable polymers include polycarbonate (PC); polysulfone (PSU); poly(methyl methacrylate) (PMMA) (also known as acrylic); and cyclic olefin co-polymer (COC). Polymers can be formed into preforms using cast-moulding and moulds can be designed such that the resulting first preform will comprise a wall and a channel extending axially within the wall.

In embodiments of the invention, the step of providing a first preform comprises providing a first preform comprising an internal wall.

In such embodiments, the first preform comprises an internal wall dividing the first preform into multiple lumens. After drawing the first preform, the resulting first tube will comprise multiple lumens that can be used as separate instrument channels.

In embodiments of the invention, the step of segmenting the first tube comprises laser cutting the tube to form the interlocking segments.

The laser cutting removes portions of the first tube wall to form the interlocking segments. Interlocking features are cut into the surface and through the wall of the first tube. Details of the structure or pattern of the interlocking features are discussed further below, but the features result in interlocking segments integrally formed into a surgical device.

The laser cutting may comprise the further steps of causing the first tube to move axially relative to a beam of the laser, and also causing the first tube to rotate about its axis.

The laser may be a continuous wave laser or a pulsed laser depending on the material of the first preform and resultant first tube. The power, wavelength and pulse duration can be selected to achieve an optimum cut. A low average power, short pulse laser may be suitable for cutting glass or polymer materials. The nominal path of the laser beam will intersect the wall of the first tube at a first intersection point and a second intersection point. The first intersection point is closer to the laser source than the second intersection point. The laser can be operated or focussed to only cut through the wall at the first intersection point. Alternatively, or in addition, a shield rod may be inserted internally to the first tube to prevent the laser beam from reaching the second intersection point.

In embodiments of the invention, the method further comprises the steps of: supporting the plurality of interlocking segments; applying axial compression to the plurality of interlocking segments; and feeding a tendon through the channel of the first tube.

Following the segmenting of the first tube, feeding a tendon through the axial channel of the first tube can be difficult due to relative hinging or rotation of adjacent segments. Supporting the plurality of interlocking segments under axial compression can hold the segments in a nominal position such that the rotation or hinging between adjacent segments is reduced or minimised. Under compression, the plurality of interlocking segments may lie in a straight configuration similar to that of the first tube prior to the segmenting step. This can simplify the step of feeding the tendon through the axial channel.

Following insertion, the tendon can be secured at a distal end of the plurality of interlocking segments. The tendon can be secured to the distal end by adhesive or welding, such as laser welding, or mechanical means. The tendon may comprise a ball-head pin to aid adhesion. Following insertion and securing of the tendon, the axial compression can be released from the surgical device. The surgical device can then be manipulated or bent by applying tension to the tendon. Applying tension to the tendon can bend the surgical device by causing adjacent segments to hinge or rotate according to the force resulting from the tension of the tendon.

As mentioned above, there may be more than one channel. One tendon can be fed into each channel and secured at the distal end. In this way, multiple tendons can control the bending of the surgical device in one or two degrees of freedom. Axial channels may be arranged within the wall of the first tube, in pairs, with one of each pair on opposite sides of the first tube. Tendons fed into such channels can form antagonistic pairs of tendons. Applying tension to each one of the pair of antagonistic tendons will manipulate or bend the surgical device in opposing directions. For example, in the case of two channels on opposite sides of the first tube, applying tension to a first tendon can cause the surgical device to bend in one direction. Adjacent interlocking segments hinge or rotate in a direction about a rotation axis. Applying tension to a second tendon can cause the surgical device to bend in an opposite direction. Adjacent interlocking segments hinge or rotate in an opposite direction about the rotation axis.

The tendon may comprise a super-elastic nitinol cable; a liquid crystal polymer (LCP) monofilament or another suitable biocompatible material.

In embodiments of the invention, the method further comprises the steps of: providing a second preform having an axis and a wall with a channel extending axially within the wall; drawing the second preform to form a second tube having an axis and a wall with a channel extending axially within the wall and rotating either the second preform or the second tube during the drawing process; and abutting the second tube with the first tube.

The second tube is thus formed in a similar way to the first tube. However, either the second tube or second preform are rotated during the drawing process. In this way, the axial channel in the wall of the second tube extends axially along a spiral pathway within the wall of the second tube.

As with the first tube and first preform, there may be more than one channel. The number of channels in the second tube may equal the number of channels in the first tube. Each channel in the second tube will extend along a spiral pathway within the wall of the second tube.

The second tube can be a flexible shaft for supporting the plurality of interlocking segments of the first tube. The spiral path of the channel can compensate for length changes of the tendon when the surgical device is bent, particularly when there are pairs of channels with pairs of antagonistic tendons as described above. The spiral paths can facilitate accurate control of the bending of the surgical device.

In embodiments of the invention, the step of rotating comprises rotating the second preform or the second tube at a constant revolution rate. Rotating the second preform or second tube at a constant revolution rate can create a helical-channel with a constant pitch.

In embodiments of the invention, providing the second preform comprises providing a second preform comprising polymer or glass. The second preform may comprise the same material as the first preform.

In embodiments of the invention, the step of drawing the preform comprises the steps of, in any order: fibre drawing the first preform to form the first tube; and fibre drawing the first preform to form a second tube and rotating either the first preform or the second tube during the drawing of the second tube.

In such embodiments, the first preform is fibre drawn to form the first tube with no rotation applied to the first preform or first tube. The first preform is fibre drawn to form the second tube by rotating the first preform or second tube during the fibre draw. The rotation results in a channel in the wall of the second tube extending axially along a spiral pathway within a wall of the second tube. Drawing the second tube may follow drawing the first tube or vice versa. The rotation may be applied at a constant rate.

Such embodiments advantageously simplify the fabrication of the surgical device. There is also no requirement to align the spiral channel of the second tube with the axial channel of the first tube when drawing the first and second tube from the first preform in a continuous process.

In embodiments of the invention, the steps of fibre drawing the first preform to form the first tube and fibre-drawing the first preform to form the second tube, form a continuous fibre drawing process.

In such embodiments the first tube and the second tube are both formed from the first preform in a continuous fibre draw. The first tube and second tube may be drawn in a continuous process by applying or halting the rotation of the first preform or second tube appropriately.

In embodiments of the invention, the method may comprise feeding the tendon into the first tube fibre or a second tube fibre during the drawing process.

The tendon may be fed into the first tube fibre or the second tube fibre during the drawing process. The tendon may be fed into the second tube fibre during the drawing process and then fed through the first tube following forming and segmenting the first tube. This can reduce the risk of the tendon being cut during the segmenting step.

The invention will now be described by way of example only with reference to the accompanying drawings in which:

FIGS. 2a and 2b are schematic representations of the surgical device of FIG. 1 showing the device in more detail;

Figure 1:
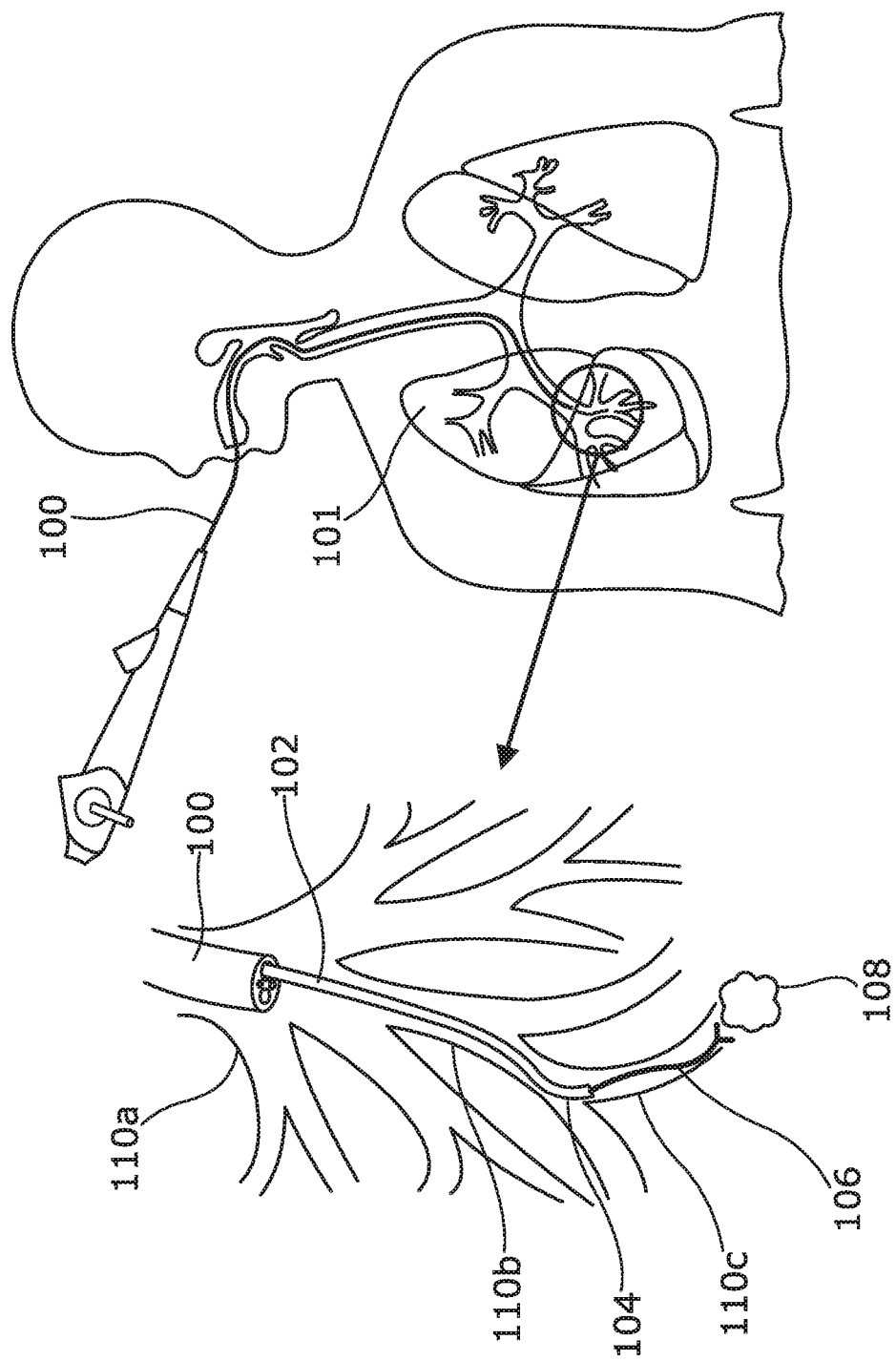
FIG. 1 is a schematic illustration of a surgical device, according to an embodiment of the first aspect of the present invention, in use during a bronchoscopic intervention.

FIG. 1 is a schematic illustration of a surgical device according to a first aspect of the present invention in use during a bronchoscopic intervention. A flexible bronchoscope 100 is inserted through a patient's mouth and into their right lung 101. The flexible bronchoscope 100 enters into a third-generation bronchiole 110a. The outer diameter of the flexible bronchoscope 100 is too narrow to travel further into the lung 101, such as into a fourth-generation bronchiole 110b or a fifth-generation bronchiole 110c. To access the higher generation bronchii, a flexible manipulator 104 housed inside the flexible bronchoscope 100 is actuated or steered by an operator and guided through the fourth-generation bronchiole 110b into the fifth-generation bronchiole 110c. A proximal end of the flexible manipulator 104 is attached to a flexible shaft 102 which follows the path taken by the flexible manipulator 104. The flexible shaft 102 and the flexible manipulator 104 both comprise an instrument channel through which an instrument 106 can pass through to reach a tissue of interest 108. The instrument 106 can be used to take a biopsy of the tissue of interest 108 or deliver an implant.

FIGS. 2a and 2b are schematic representations of a surgical device in accordance with another embodiment of the first aspect of the invention. The figures show a surgical device 204 that could be used as the surgical manipulator in the bronchoscope of FIG. 1. FIGS. 2a and 2b illustrate the surgical device 204 from a top-viewpoint and a side-viewpoint respectively.

The surgical device 204 comprises a first tube 232 having an axis 233 and a wall and two channels (not shown) extending axially within the wall. Two tendons 235a, 235b extend through the channels and are secured at a distal end of the first tube 232 by respective ball-head pins 237a, 237b.

The first tube 232 comprises a plurality of interlocking segments 234. In this embodiment, axial locks 236 comprise an axial lock component 238 and a complementary axial lock component 240. The axial lock component 238 of a first interlocking segment is engageable with the complementary axial lock component 240 of an adjacent second interlocking segment. Axial locks 236 provide axial interlocking between adjacent interlocking segments. The axial locks also provide tangential interlocking in a direction z tangential to a surface at the centre point of the axial lock 236 and perpendicular to the axis 233 of the first tube 232.

Tangential locks 242 comprise a tangential lock component 244 and a complementary tangential lock component 246. The tangential lock component 244 of the first interlocking segment is engageable with the complementary tangential lock component 246 of the second interlocking segment. The tangential locks 242 provide tangential interlocking in a direction y tangential to a surface at the centre point of the tangential lock 242 and perpendicular to the axis 233 of the first tube 232.

Figure 3A:
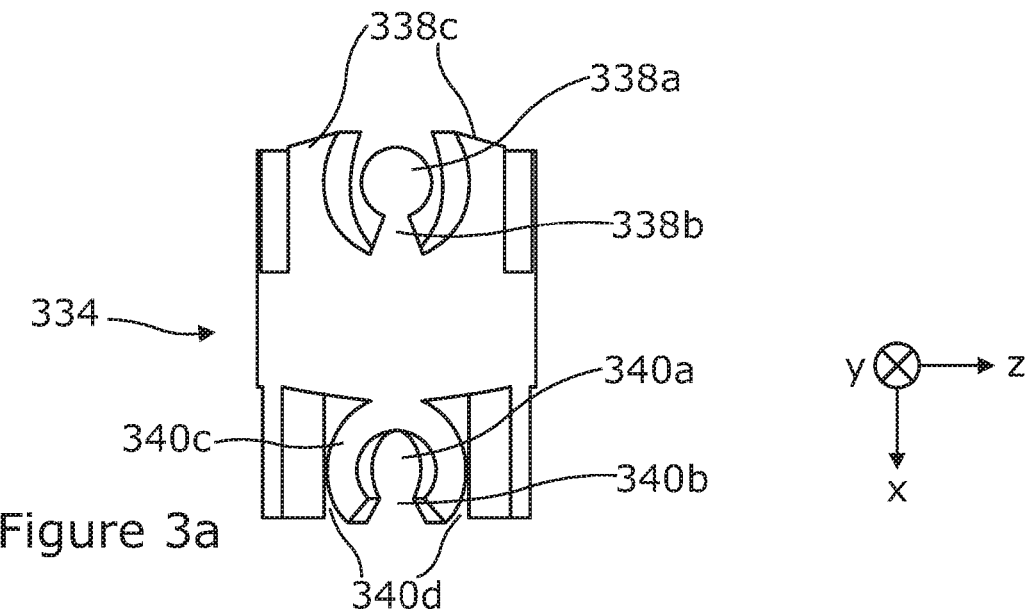
FIGS. 3a to 3c are schematic representation of interlocking segments of the surgical device of FIGS. 2a and 2b.
Figure 3B:
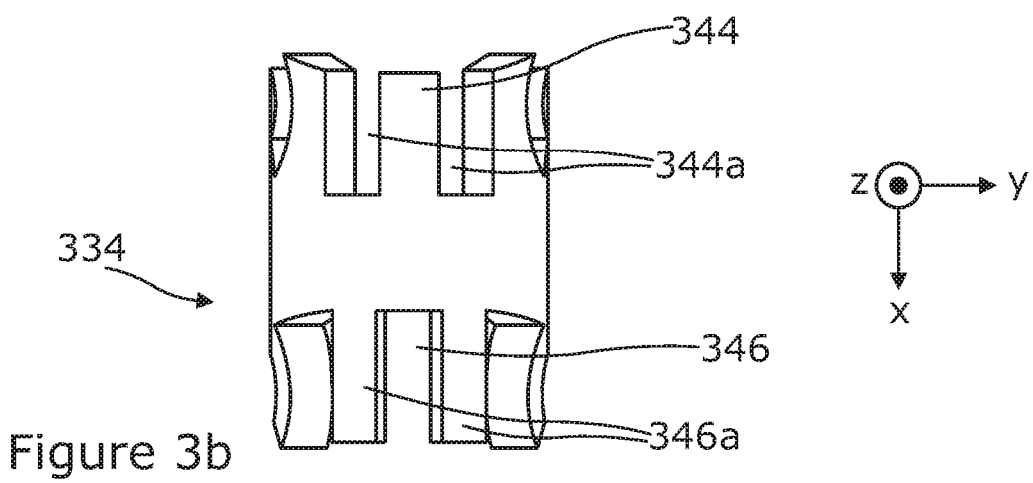
Figure 3C:
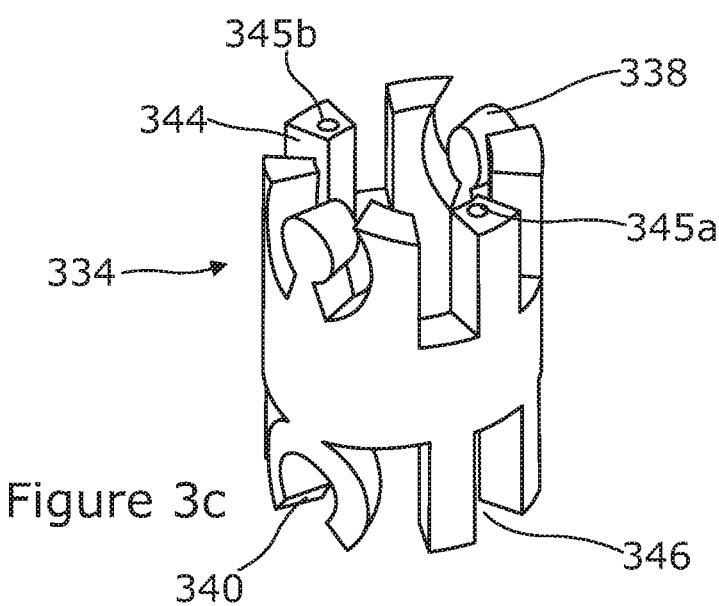

FIGS. 3a to 3c each illustrate the design of an interlocking segment 334 from the surgical device of FIGS. 2a and 2b. The axial lock component of the interlocking segment 334 comprises a head 338a and a neck 338b protruding from the head 338a. The complementary axial lock component of the interlocking segment 334 comprises a cavity 340a and an opening 340b adjacent to the cavity 340a. In this embodiment, the axial lock component further comprises two wings 338c, each wing 338c located on either side of the head 338a and neck 338b and separated by a gap. The complementary axial lock component further comprises: a C-shaped feature 340c defining an edge of the cavity; and two complementary wing features 340d, with each complementary wing feature 340d located on either side of the C-shaped feature 340c.

The head 338a and neck 338b of the axial lock component form a keyhole shape. The cavity 340a and opening 340b of the complementary axial lock component form a similar keyhole shape. A width or diameter of the head 338a is similar to but less than a width of the cavity 340a. A width of the neck 338b is narrower than a width of the opening 340b. As a result, the head 338a of a first interlocking segment can rotate inside the cavity of an adjacent second interlocking segment. The extent of rotation is defined by the difference in width between the neck 338b and the opening 340b. In this way, the first interlocking segment can rotate relative to the second interlocking segment about a rotation axis y.

The tangential lock component of the interlocking segment 334 comprises a stub 344. The complementary tangential lock component comprises a slot 346. A width of the stub 344 is similar to but less than the width of the slot 346. As a result, the stub 344 of a first interlocking segment cannot rotate inside the slot of an adjacent second interlocking segment about a static axis z. In this embodiment, the tangential lock component further comprises two slots 344a, each slot 344a located on either side of the stub 344 of the tangential lock component. The complementary tangential lock component further comprises two stubs 346a, each stub 346a located on either side of the slot 346 of the complementary tangential lock component.

FIG. 3c illustrates that the interlocking segment 334 comprises a pair of axial lock components 338; a pair of complementary axial lock components 340; a pair of tangential lock components 344; and a pair of complementary tangential lock components 346. The two channels 345a, 345b that accommodate the tendons of FIG. 2 are also visible in the figure. In this embodiment, the channels extend axially through the stubs 344 of the tangential lock component.

Figure 3D:
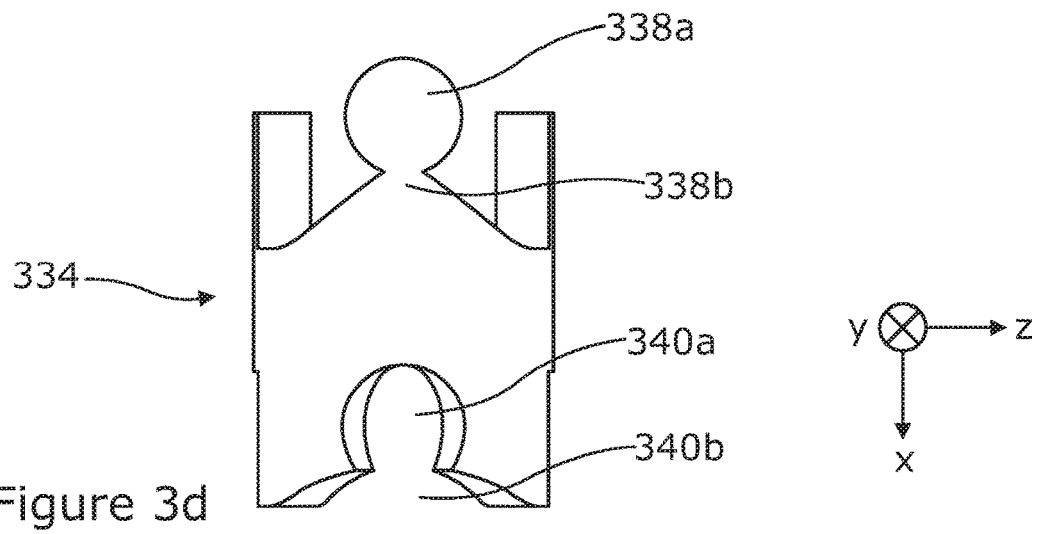
FIGS. 3d to 3f illustrate a design of an interlocking segment according to a further embodiment of the present invention.
Figure 3E:
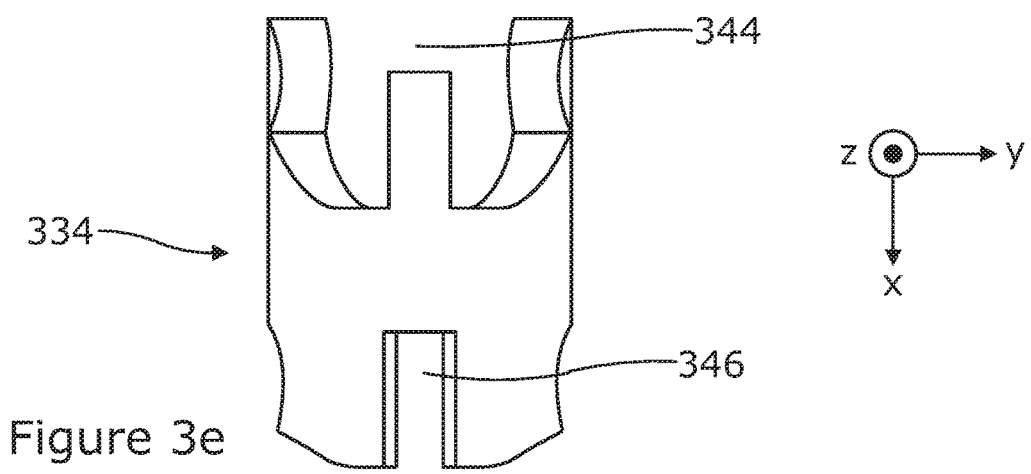
Figure 3F:
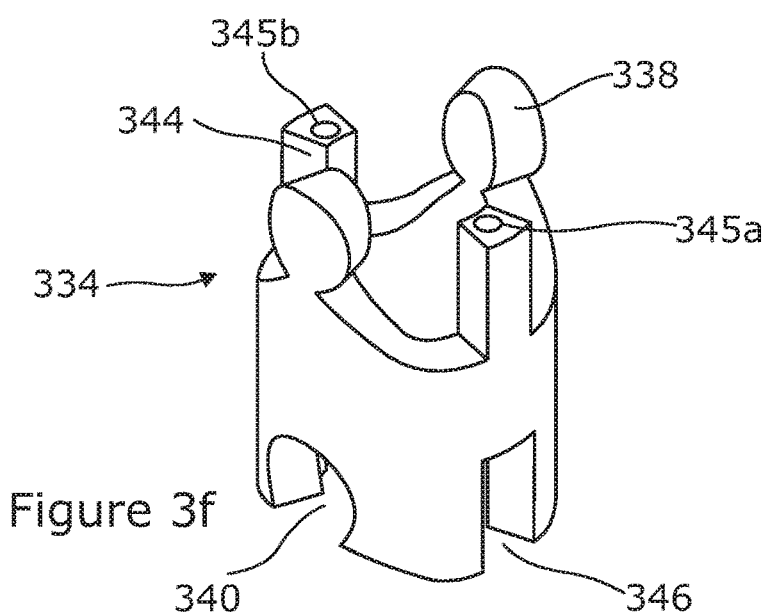

FIGS. 3d to 3f illustrate a design of an interlocking segment 334 according to further embodiment of the invention. The design is similar to that of FIGS. 3a to 3c except that the axial lock in this embodiment does not comprise the additional features of the wings, the complementary wing features, and the C-shape feature, and the tangential lock does not comprise the additional two stubs and two slots.

Returning to FIG. 2, in this embodiment, the axial lock component 238 and complementary axial lock component 240 of each interlocking segment 234 are axially aligned with one another. As a result, the axial locks 236 between each of the adjacent interlocking segments all have parallel rotation axes, y. The axial locks therefore give rise to bending of the surgical device in one degree of freedom, defined by a plane perpendicular to the axes of rotation (x/z).

Figure 4A:
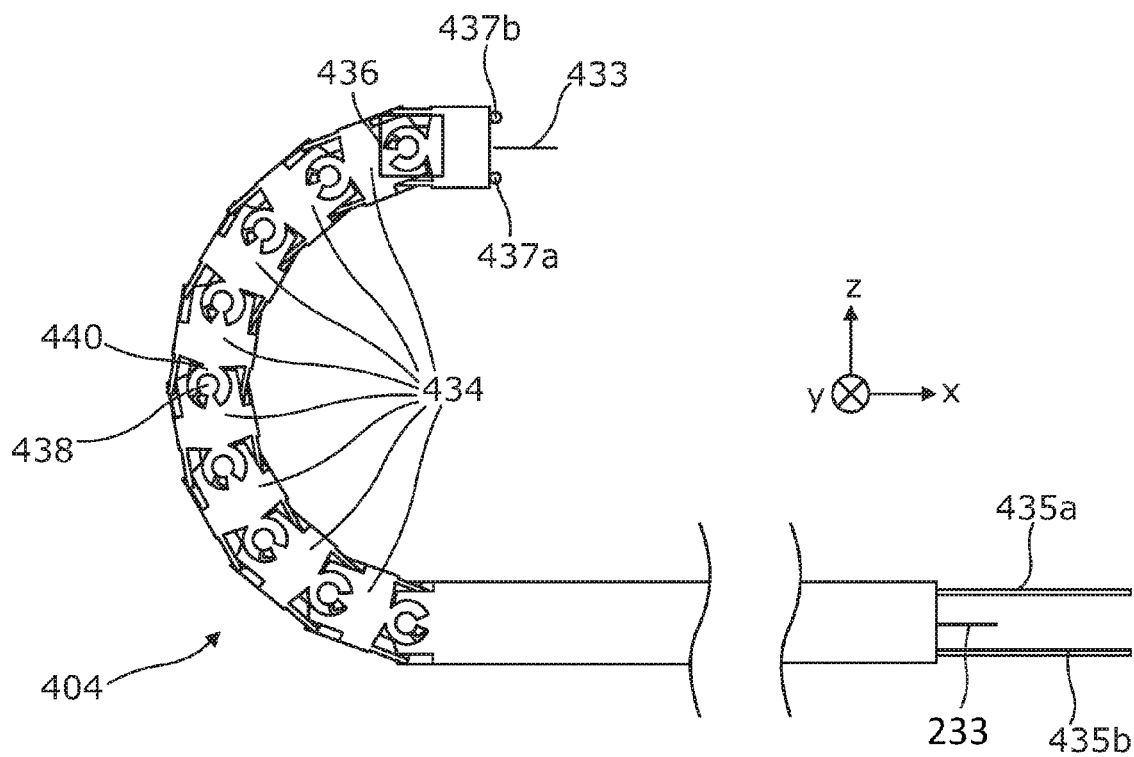
FIG. 4a is a schematic representation of the surgical device of FIG. 2a in a bent configuration.

FIG. 4a is a schematic representation of the surgical device of FIG. 2a in a bent configuration. In this embodiment, each of the plurality of interlocking segments 434 is rotated or hinged relative to their adjacent segments. The rotation is facilitated by the axial locks 436 in which the head and neck of each axial lock component 438 is rotated inside the cavity and opening 440 of an adjacent interlocking segment. The figure illustrates the maximum degree of bending in which the rotation in each axial lock 436 is at a maximum. The maximum rotation provided by each axial lock 436 is determined by a relative width difference between the neck of the axial lock component 438 and the opening of the complementary axial lock component 440. The abuttal of a side of the neck against a side of the opening limits the extent of rotation in both directions of rotation.

Figure 4B:
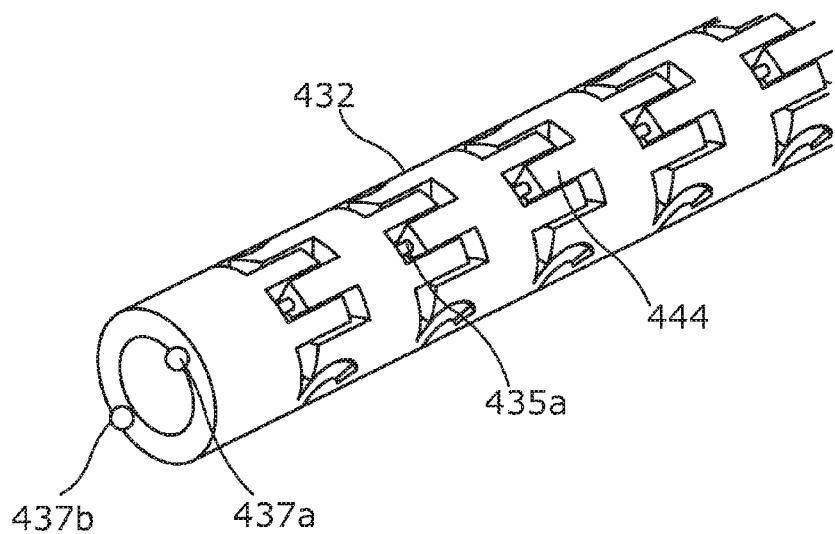
FIG. 4b is a schematic representation of the surgical device of FIG. 2a in a straight configuration with two tendons extending through two channels.

The rotation can be actuated by the tendons 435a, 435b fed though the channels of the surgical device 404. In this embodiment, a pair of antagonistic tendons 435a, 435b are accommodated in two channels extending axially within the wall on opposite sides of the surgical device 404. In this embodiment, the channels and tendons 435a, 435b extend axially within the wall through the stubs 444 of the tangential lock components of each interlocking segment, as illustrated in FIG. 4b. The tendons 435a, 435b are secured at the distal end of the first tube 432 by ball head pins 437a, 437b.

In FIG. 4a, the tendons 435a, 435b run within the wall along the inner radius of curvature and outer radius curvature of the surgical device 404 (as illustrated). In the same way as FIG. 4b, the tendons run through the stubs of each interlocking segment 434 on both sides of the surgical device 404. By applying tension to the tendon 435a, running within the wall on the inner radius of curvature, the surgical device bends as shown. Releasing the tension and applying tension to the other tendon 435b can return the device to the orientation of FIG. 2a and applying further tension can bend the surgical device in the opposite direction (−z) to that shown in FIG. 4.

Figure 5A:
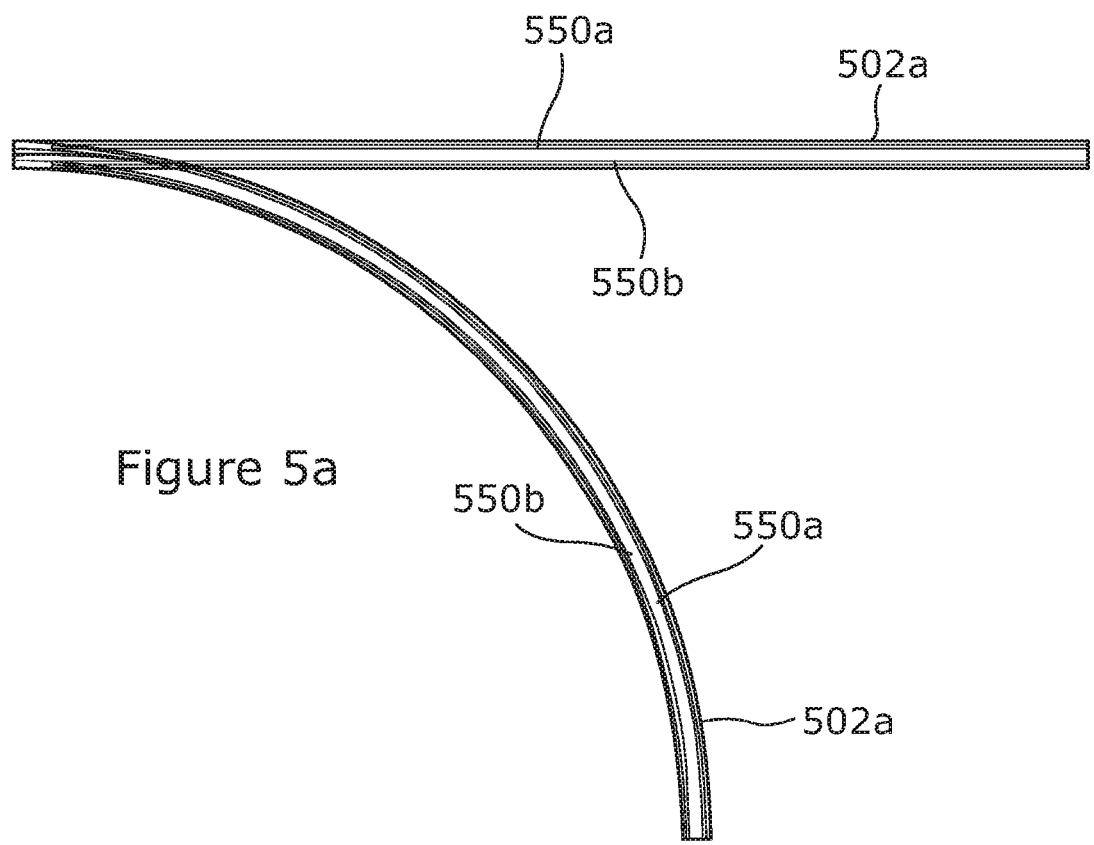
FIG. 5a is a schematic representation of a second tube comprising straight channels.
Figure 5B:
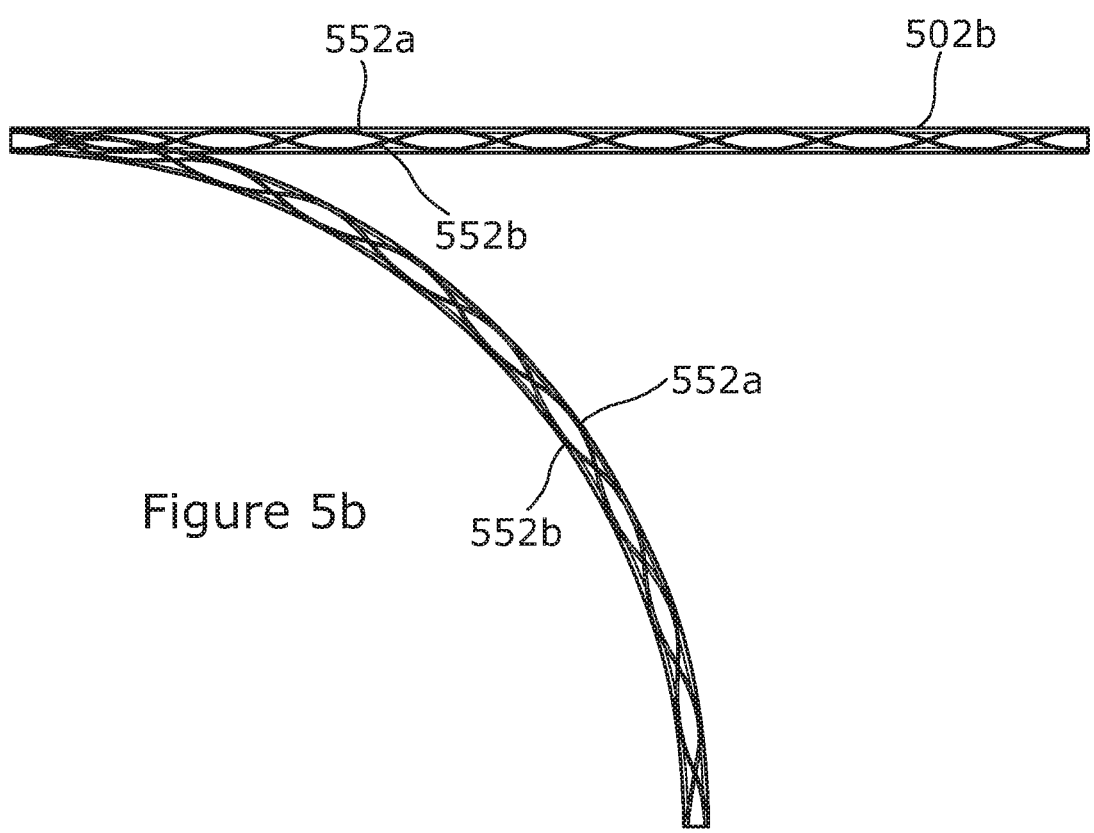
FIG. 5b is a schematic representation of a second tube comprising spiral channels.

FIGS. 5a and 5b are schematic representations of second tubes 502a, 502b with respectively straight and spiral channels extending axially within a wall of the tube. The second tubes 502a, 502b can be used as the flexible shaft in the surgical device of FIG. 1, having a flexible manipulator attached to a distal end of the second tube 502.

FIG. 5a illustrates a second-tube 502a comprising two straight channels 550a, 550b extending axially within a wall of the second tube 502a. The second tube 502a is illustrated in both a straight and bent configuration. The straight channels 550a, 550b can accommodate tendons (not shown). In the straight configuration, the tendons in each of the straight channels 550a, 550b will be the same length. When the flexible second-tube 502a bends into the bent configuration, the straight channel 550b along the inner radius of curvature will become shorter than the straight channel 550a along the outer radius of curvature. The tendon running through the straight channel 550b along the inner radius of curvature can become slack. At the same time, the tendon running through the straight channel 550a along the outer radius of curvature can become taught. This unwanted tensioning/slackening can influence the bending of a flexible manipulator (such as the one in FIG. 2) attached to the distal end of the second tube 502. Bending of the second tube 502 can be unpredictable as the second tube 502 follows the flexible manipulator through intricate human passage-ways. The unwanted tendon length changes can damage instruments or even harm patients.

FIG. 5b illustrates a schematic representation of a second-tube 502b for use in a surgical device according to another embodiment of the present disclosure. In this embodiment, the second-tube 502b comprises spiral channels 552a, 552b extending axially within a wall of the second tube 502b. The second tube 502b is illustrated in both a straight and bent configuration. The spiral channels 552a 552b can accommodate tendons (not shown). The spiral channels 552a 552b are substantially the same length as each other in both the straight and bent configurations. As a result, the undesirable effects of tendon tensioning and unwanted tendon length changes upon bending of the second tube 502b is reduced in this embodiment.

Figure 6:
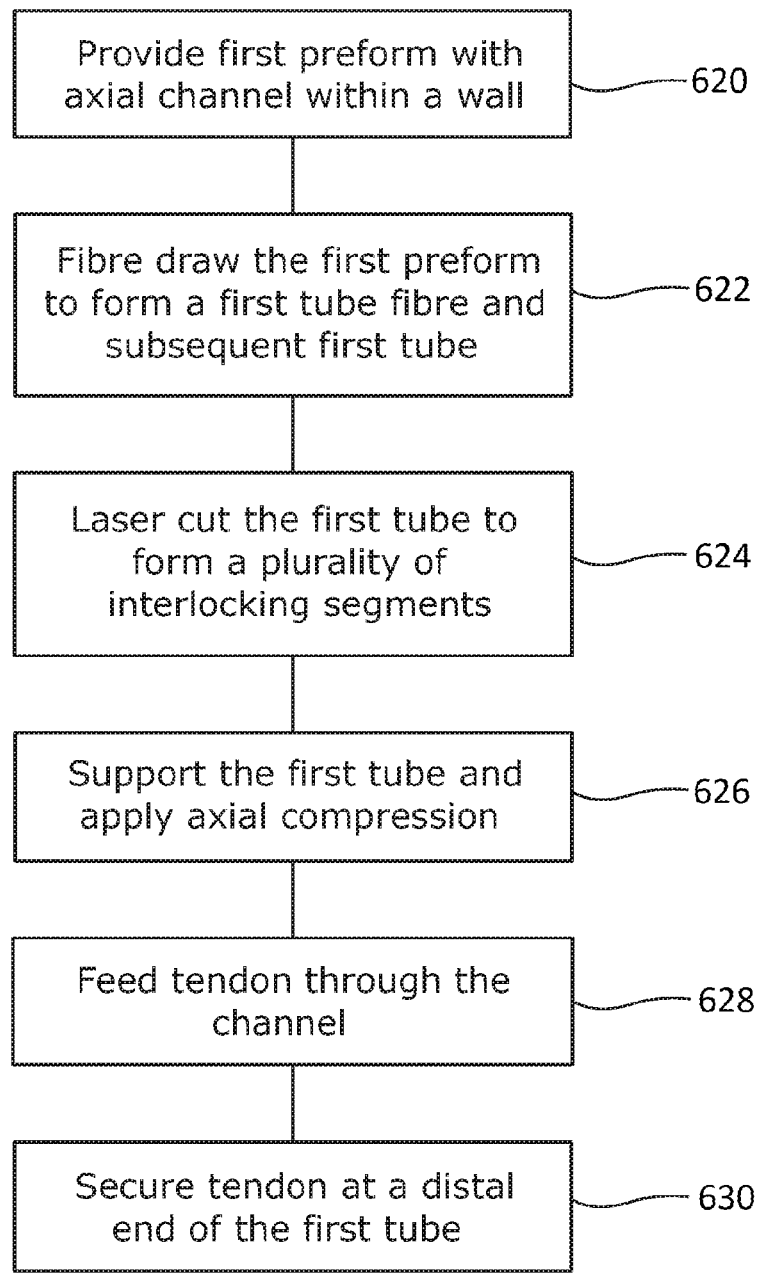
FIG. 6 is a representation of a method of fabricating the surgical device of FIG. 1 according to an embodiment of the second aspect of the invention.

FIG. 6 is a schematic illustration of a method of fabricating a surgical device according to an embodiment of the second aspect of the invention, such as the flexible manipulator of FIG. 1. Reference is also made to FIG. 2 in respect of some of the apparatus fabricated by the method.

The method of FIG. 6 includes a first step 620 of providing a first preform with an axial channel within a wall of the first preform. In a second step 622, the first preform is drawn using a fibre drawing process to form a first tube fibre. The first tube fibre is subsequently cut into lengths to form a first tube 232. The first tube 232 comprises a scaled version of the preform with a scaled channel within a wall of the first tube 232. In a third step 624, the first tube 232 is segmented by laser cutting to form a plurality of interlocking segments 234. In a fourth step 626, the first tube 232 is supported before applying axial compression to the ends of the first tube 232. In a fifth step 628 a tendon is fed through the axial channel of the first tube 232. In a seventh step 630 the tendon is secured at a distal end of the first tube 232.

The invention claimed is:

1. A method of fabricating a surgical device comprising the steps of:
   providing a first preform having an axis and a wall with a channel extending axially within the wall;
   drawing the first preform to form a tube having an axis and a wall with a channel extending axially within the wall;
   segmenting the tube into a plurality of interlocking segments;
   providing a second preform having an axis and a wall with a channel extending axially within the wall;
   drawing the second preform to form a second tube having an axis and a wall with a channel extending axially within the wall and rotating either the second preform or the second tube during the drawing process; and
   abutting the second tube to the first tube.

2. The method of claim 1, wherein the step of rotating comprises rotating the second preform or the second tube at a constant revolution rate.

3. The method of claim 1, wherein providing the second preform comprises providing a second preform comprising polymer or glass.

4. The method of claim 1, wherein: (a) the step of drawing the first preform comprises drawing the first preform using a fibre drawing process; and/or the step of providing a first preform comprises providing a first preform comprising polymer or glass.

5. The method of claim 1, wherein the step of providing a first preform comprises providing a first preform comprising an internal wall.

6. The method of claim 1, wherein the step of segmenting the first tube comprises laser cutting the tube to form the interlocking segments.

7. The method of claim 1, wherein the step of segmenting the first tube comprises a mechanical cutting process, a chemical etching process and/or a lithography process.

8. The method of claim 1, further comprising the steps of:
supporting the plurality of interlocking segments;
applying axial compression to the plurality of interlocking segments; and
feeding a tendon through the channel of the first tube.

9. A method of fabricating a surgical device comprising the steps of:
providing a first preform having an axis and a wall with a channel extending axially within the wall;
drawing the first preform using a fibre drawing process to form a tube having an axis and a wall with a channel extending axially within the wall; and
segmenting the tube into a plurality of interlocking segments;
wherein the step of drawing the preform comprises the steps of, in any order:
fibre drawing the first preform to form the first tube; and
fibre drawing the first preform to form a second tube and rotating either the first preform or the second tube during the drawing of the second tube.

10. The method of claim 9, wherein the steps of fibre drawing the first preform to form the first tube and fibre-drawing the first preform to form the second tube, form a continuous fibre drawing process.

* * * * *